(12) United States Patent
Robles et al.

(10) Patent No.: US 11,752,046 B2
(45) Date of Patent: *Sep. 12, 2023

(54) ABSORBENT ARTICLE WITH DUAL CORE

(71) Applicant: The Procter & Gamble Company, Cincinnati, OH (US)

(72) Inventors: Miguel Alvaro Robles, Wyoming, OH (US); Bruce William Lavash, West Chester, OH (US); Sion Agami, Mason, OH (US); John Lee Hammons, Hamilton, OH (US)

(73) Assignee: The Procter and Gamble Company, Cincinnati, OH (US)

(*) Notice: Subject to any disclaimer, the term of this patent is extended or adjusted under 35 U.S.C. 154(b) by 838 days.

This patent is subject to a terminal disclaimer.

(21) Appl. No.: 16/519,281

(22) Filed: Jul. 23, 2019

(65) Prior Publication Data
US 2019/0374408 A1  Dec. 12, 2019

Related U.S. Application Data

(63) Continuation of application No. 14/630,673, filed on Feb. 25, 2015, now Pat. No. 10,398,610.
(Continued)

(51) Int. Cl.
*A61F 13/15* (2006.01)
*A61F 13/532* (2006.01)
(Continued)

(52) U.S. Cl.
CPC .......... *A61F 13/532* (2013.01); *A61F 13/533* (2013.01); *A61F 13/535* (2013.01);
(Continued)

(58) Field of Classification Search
CPC .. A61F 13/532; A61F 13/5323; A61F 13/533; A61F 2013/530481; A61F 2013/530583; A61L 15/24; A61L 15/425
See application file for complete search history.

(56) References Cited

U.S. PATENT DOCUMENTS 5,147,345 A  9/1992  Lavon
5,219,341 A  6/1993  Serbiak
(Continued)

FOREIGN PATENT DOCUMENTS

JP  2005152250  6/2005
JP  2007061473  3/2007
(Continued)

OTHER PUBLICATIONS

All Office Actions, U.S. Appl. No. 14/630,673.
(Continued)

*Primary Examiner* — Jacqueline F Stephens
(74) *Attorney, Agent, or Firm* — William E. Gallagher; Amanda Herman Berghauer

(57) ABSTRACT

The absorbent article includes a topsheet having a body contacting surface, a backsheet joined to said topsheet, and an absorbent core disposed between the topsheet and the backsheet, wherein the absorbent core has a first absorbent core having a first area and a second area, wherein the first absorbent core and the second absorbent core are vertically arranged, wherein the second absorbent core at least partially covers the second area of the first absorbent core, and wherein the first absorbent core and the second absorbent core have different compositions.

2 Claims, 11 Drawing Sheets

Related U.S. Application Data

(60) Provisional application No. 61/992,232, filed on May 13, 2014.

(51) Int. Cl.
    *A61L 15/24*           (2006.01)
    *A61L 15/60*           (2006.01)
    *A61L 15/42*           (2006.01)
    *A61F 13/535*          (2006.01)
    *A61F 13/533*          (2006.01)
    *A61F 13/53*           (2006.01)

(52) U.S. Cl.
    CPC .......... *A61F 13/5323* (2013.01); *A61L 15/24* (2013.01); *A61L 15/425* (2013.01); *A61L 15/60* (2013.01); *A61F 2013/530481* (2013.01); *A61F 2013/530583* (2013.01)

(56) References Cited

U.S. PATENT DOCUMENTS

| | | |
|---|---|---|
| 5,242,435 A | 9/1993 | Murji |
| 5,306,267 A | 4/1994 | Hahn |
| 5,387,207 A | 2/1995 | Dyer |
| 5,649,916 A | 7/1997 | Dipaima |
| 5,807,362 A | 9/1998 | Serbiak |
| 5,830,202 A | 11/1998 | Bogdanski |
| 5,899,893 A | 5/1999 | Dyer |
| 6,245,410 B1 | 6/2001 | Haehnle |
| 6,534,149 B1 | 3/2003 | Daley et al. |
| 6,570,057 B1 | 5/2003 | Schmidt |
| 6,582,411 B1 | 6/2003 | Carstens |
| 6,649,809 B2 | 11/2003 | Fields |
| 6,821,270 B2 | 11/2004 | Rosenfeld |
| 7,235,708 B2 | 6/2007 | Guidotti |
| 9,649,228 B2 | 5/2017 | Robles |
| 10,398,610 B2 * | 9/2019 | Robles .................. A61L 15/60 |
| 2003/0153890 A1 | 8/2003 | Rosenfeld |
| 2003/0181115 A1 | 9/2003 | Nagasuna et al. |
| 2004/0030313 A1 * | 2/2004 | Watanabe ......... A61F 13/53747 |
| | | 604/385.01 |
| 2004/0162536 A1 | 8/2004 | Becker |
| 2006/0184150 A1 | 8/2006 | Noel |
| 2007/0225669 A1 | 9/2007 | Dyer |
| 2008/0103467 A1 | 5/2008 | Wallstrom et al. |
| 2010/0137773 A1 | 6/2010 | Gross et al. |
| 2013/0116646 A1 | 5/2013 | Robles |
| 2014/0336606 A1 | 11/2014 | Bewick-sonntag |
| 2015/0209200 A1 | 7/2015 | Fouillet et al. |

FOREIGN PATENT DOCUMENTS

| | | |
|---|---|---|
| JP | 2009100846 | 5/2009 |
| JP | 2009207598 | 9/2009 |
| JP | 2009261777 A1 | 11/2009 |
| JP | 4508861 | 5/2010 |
| JP | 4912069 | 1/2012 |
| WO | WO0063487 A1 | 10/2000 |
| WO | WO0135886 A1 | 5/2001 |
| WO | WO2012102057 A1 | 8/2012 |

OTHER PUBLICATIONS

AA908 Search Report and Written Opinion for PCT/US2015/029818 dated Jul. 16, 2015.

All Office Actions for U.S. Appl. No. 13/672,499, filed Nov. 8, 2012.

All Office Actions for U.S. Appl. No. 15/493,622, filed Apr. 21, 2017.

* cited by examiner

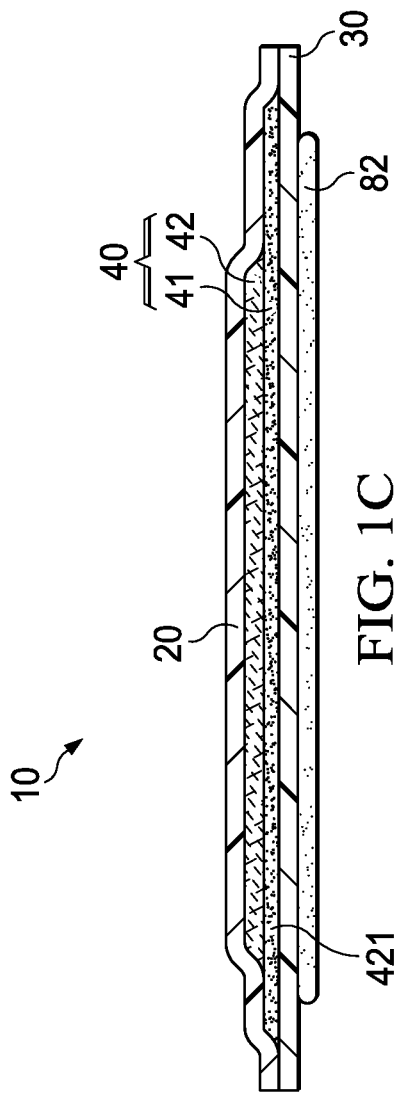
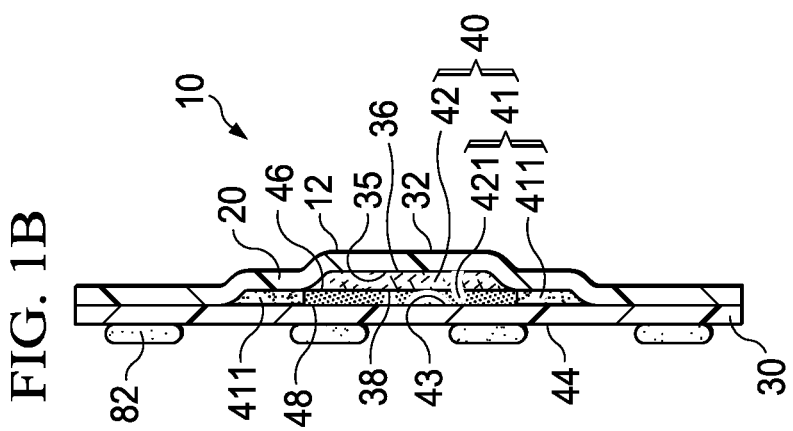

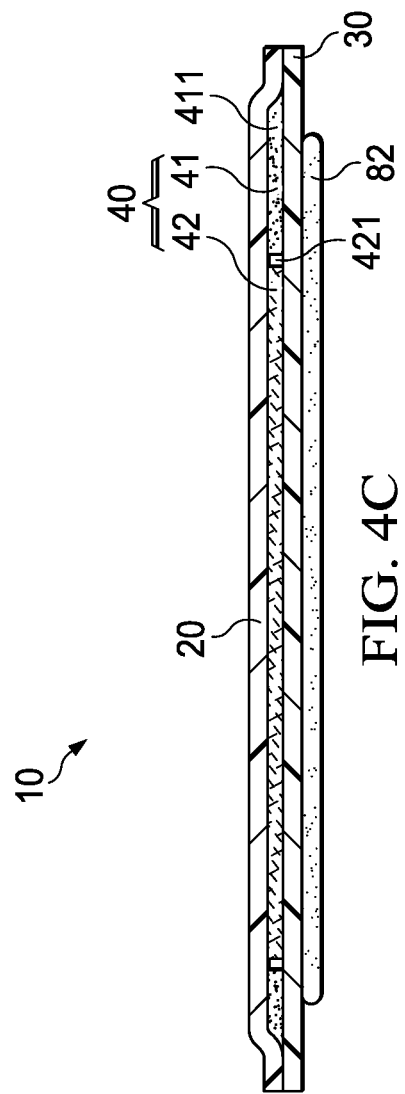
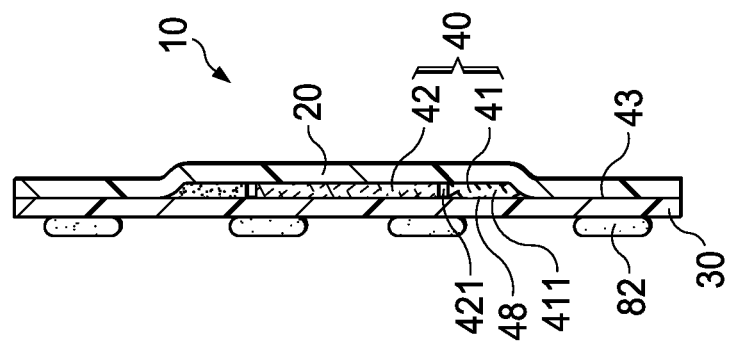

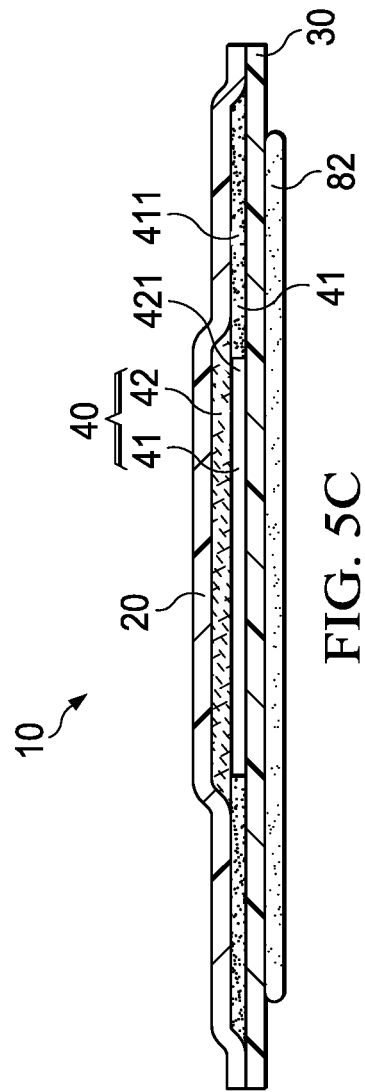
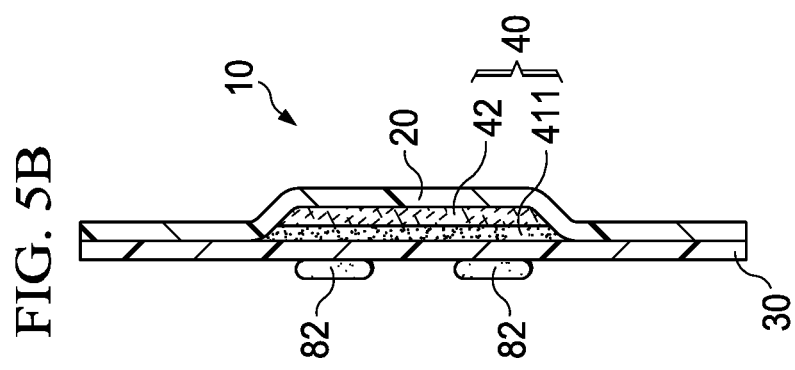

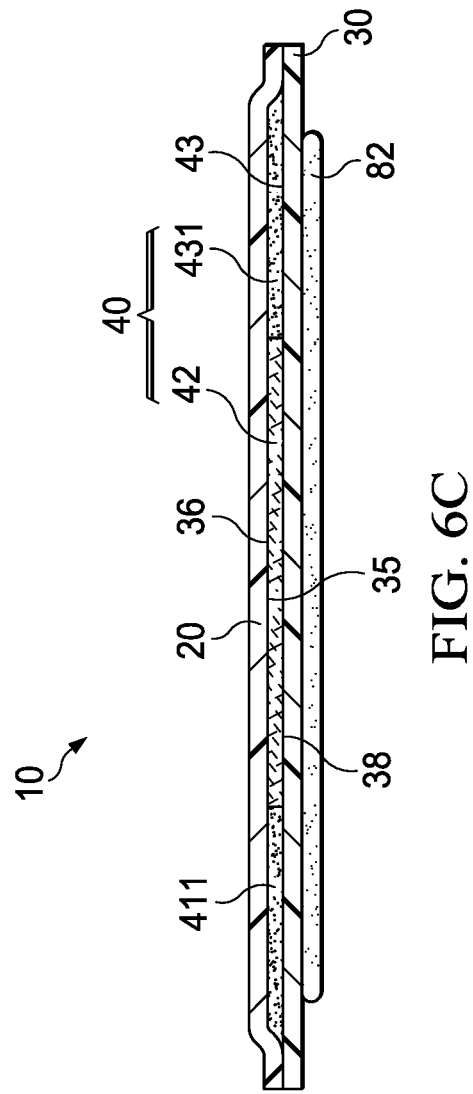
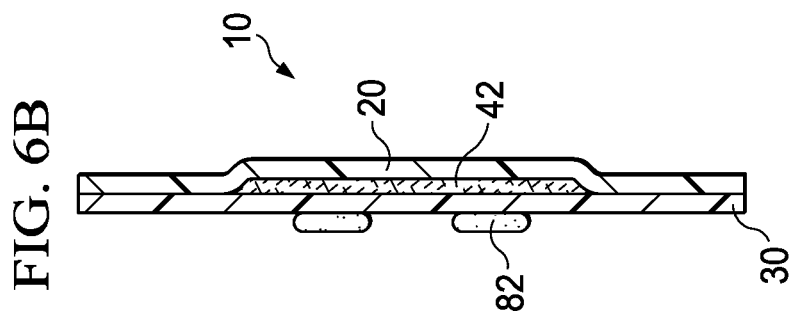

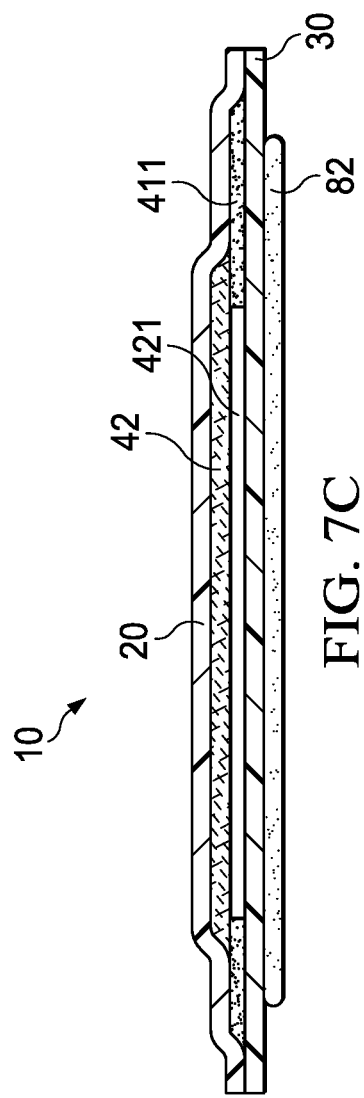
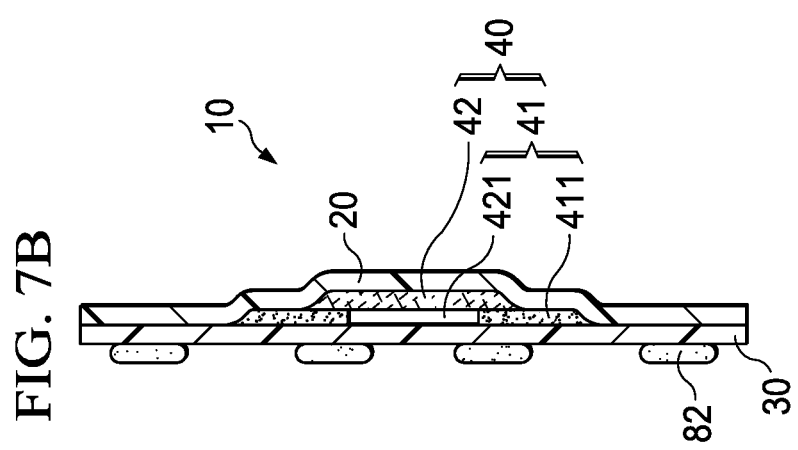

ABSORBENT ARTICLE WITH DUAL CORE

FIELD OF INVENTION

This application relates to absorbent articles, such as sanitary napkins, for the absorption of menses, diapers, adult incontinence products. More particularly, the present invention relates to absorbent articles utilizing multiple absorbent cores which is cost effective without compromising absorbency performance as well as comfort.

BACKGROUND OF THE INVENTION

Absorbent articles, such as sanitary napkins, diapers, adult incontinence products, and the like, are designed to be worn in close proximity to the crotch of the wearer. Absorbent articles need to provide for fluid acquisition and retention and need to be comfortable to wear, and usually comprise an absorbent structure having the capacity to acquire large amount of liquid under a short period of time.

Upon usage of such absorbent articles, it is desirable that they are thin and discreet to wear, and that they at the same time rapidly can acquire and store a large amount of liquid discharged during a short period of time and then store this liquid in the article.

One method to improve absorbency is to increase the width or thickness of the absorbent article. However, this approach may compromise with less comfortable pad for the consumer as the body is naturally narrow in the front region and becomes broader towards the back while the pudendal region is found in the front and most of the discharge exits the body in the front region. This creates a tradeoff between comfort and increased protection.

Another approach to improve absorbency is to adopt multiple core layers where at least an additional absorbent core is placed on a bottom absorbent core to cover at least a partial region of a surface of the bottom absorbent core which requires higher absorbent capacity than other regions. This approach may not be cost effective by using extra absorbent core material as the entire region having multiple core layers may not require the increased absorbent capacity resulted from employing the multiple core layers.

Accordingly, there is a continuing need for an absorbent article which is cost effective while not sacrificing absorbency and comfort.

SUMMARY OF THE INVENTION

The present invention provides an absorbent article having a longitudinal centerline, a transverse centerline and a central point where the longitudinal centerline and the transverse centerline cross, comprising a liquid permeable topsheet, a liquid impermeable backsheet joined to the topsheet, an absorbent core disposed between the topsheet and the backsheet, wherein the absorbent core comprises a first absorbent core comprising a first area and a second area wherein the second area has a lower absorption capacity than the first area, and a second absorbent core having a periphery, wherein the first absorbent core and the second absorbent core are vertically arranged, wherein the second absorbent core at least partially covers the second area of the first absorbent core, wherein the first absorbent core and the second absorbent core are different at least in their composition, density, absorption capacity, opacity, color, flexibility, or resistance to compression or bunching.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 1B is a cross section of an absorbent article as indicated by section 1B-1B of FIG. 1A.

FIG. 1C is a cross section of an absorbent article as indicated by section 1C-1C of FIG. 1A.

FIG. 4B is a cross section of an absorbent article as indicated by section 4B-4B of FIG. 4A when a second area of a first absorbent core is a void area.

FIG. 4C is a cross section of an absorbent article as indicated by section 4C-4C of FIG. 4A when a second area of a first absorbent core is a void area.

FIG. 5B is a cross section of an absorbent article as indicated by section 5B-5B of FIG. 5A when a second area of a first absorbent core is a void area.

FIG. 5C is a cross section of an absorbent article as indicated by section 5C-5C of FIG. 5A.

FIG. 6B is a cross section of an absorbent article as indicated by section 6B-6B of FIG. 6A when a second area of a first absorbent core is a void area.

FIG. 6C is a cross section of an absorbent article as indicated by section 6C-6C of FIG. 6A.

FIG. 7B is a cross section of an absorbent article as indicated by section 7B-7B of FIG. 7A.

FIG. 7C is a cross section of an absorbent article as indicated by section 7C-7C of FIG. 7A.

DETAILED DESCRIPTION OF THE INVENTION

Figure 1A:
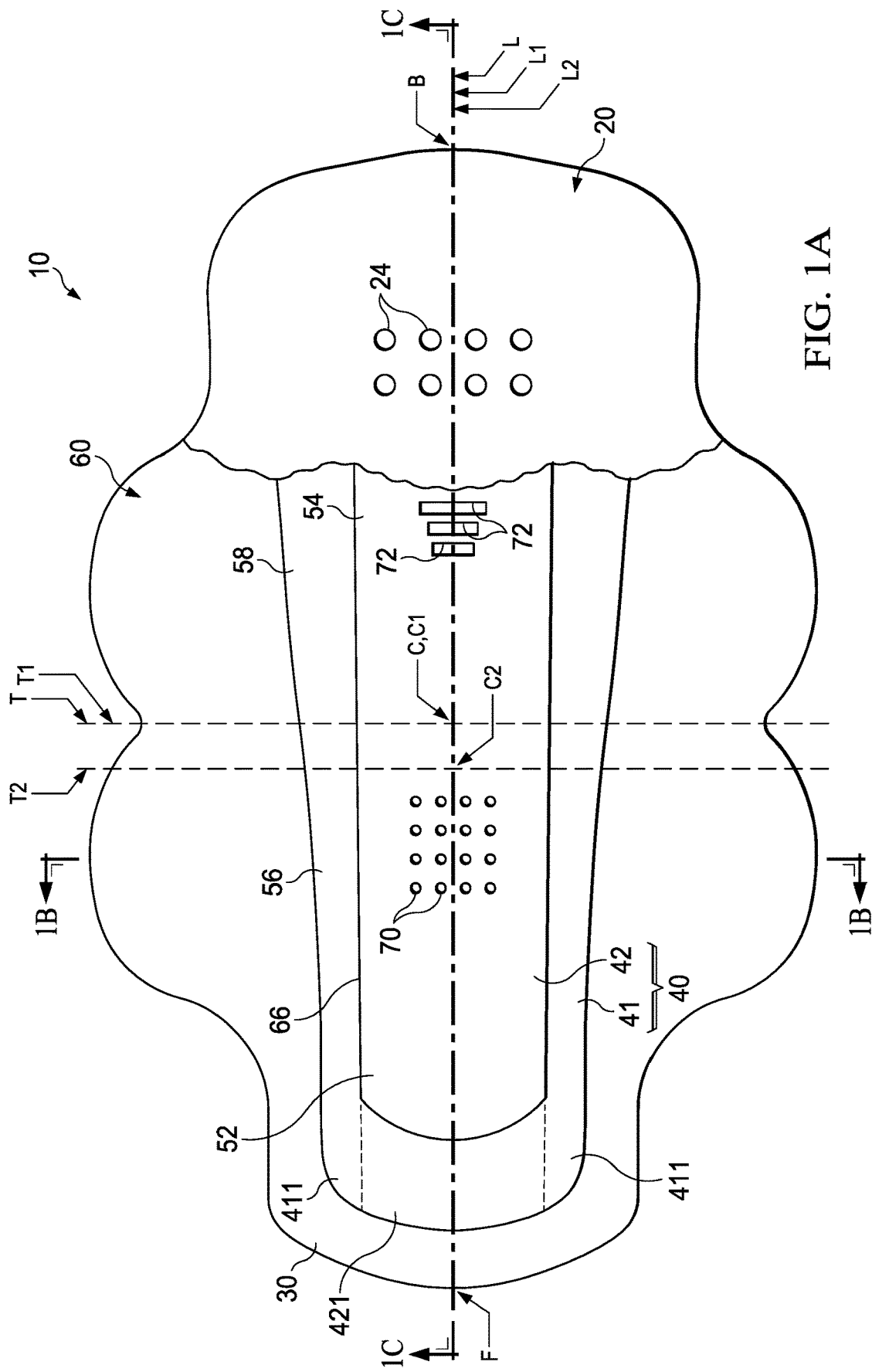
FIG. 1A is a plan view of an embodiment of an absorbent article according to the present invention.

As used herein, the term "absorbent articles" includes disposable articles such as sanitary napkins, panty liners, diapers, adult incontinence articles, and the like.

As used herein, the term "absorbent core" refers to a component of an absorbent article that is primarily responsible for the liquid handling properties of the article, including acquiring, distributing, and storing body liquids. As such, the absorbent core typically does not include the topsheet or backsheet of the absorbent article.

As used herein, the term "asymmetric" means having no symmetry about at least one axis.

As used herein, the terms "body liquid", "body liquids", "body fluids", or "body exudates" include, but are not limited to menses, vaginal discharges, blood, sweat, urine and combinations of these substances.

As used herein, the term "flexible" refers to materials which are compliant and readily conform to the general shape and contours of the wearer's body under normal body-imposed forces.

As used herein, the term "foam" is synonymous with the term "cellular polymer", which includes materials having a significant void volume, typically greater than 75%. "Open-celled" foams further have a reticulated internal structure disposed therein comprising relatively thin "strut" elements interconnected and forming cells or pores providing for fluid communication throughout the structure.

As used herein, "hydrophilic" refers to a material or substance having affinity for water or aqueous fluids. In general, a hydrophilic surface will have a contact angle with water of less than 60°, or even less than 30°.

As used herein, the term "inorganic" refers to a material which is not organic in nature. As used herein, the term "organic" refers to compounds of carbon.

As used herein the term "joined" refers to the condition where a first member is attached, or connected, to a second member either directly or indirectly. Where the first member is attached, or connected, to an intermediate member which in turn is attached, or connected, to the second member, the first member and second member are joined indirectly.

As used herein, the term "layer" refers to a three dimensional structure having two dimensions that are substantially greater than the third dimension. The term layer is not limited to single layers or sheets of material. Thus a layer may comprise laminates or combinations of several sheets or webs of the requisite type of materials. Accordingly, the term "layer" includes the terms "layers" and "layered."

As used herein, the term "microfibers" refers to fibers having an average effective diameter of 0.1 micron to 6 microns and an aspect ratio of at least 100. The aspect ratio of a microfiber is the contour length of the fiber divided by the average effective diameter of the fiber. The contour length of a fiber is the length of the fiber in a substantially straightened condition. Long microfibers can have aspect ratios which exceed $1\times10^{12}$. The microfiber may be of any configuration, including but not limited to straight, curled, kinked, crimped, and combinations thereof. The cross sectional area of the microfiber orthogonal to its contour length at any point may have any geometric shape, including but not limited to circular (round), square, flat, oval, star-shaped, irregular, and combinations thereof. For fibers having a non-circular cross section, the effective diameter is the diameter of a circle having a cross sectional area equal to that of the fiber. Microfibers may comprise any material, including but not limited to natural polymers, synthetic polymers, minerals, glass, ceramics, metals, vegetable matter, animal matter, carbon, and combinations thereof. A sample of microfibers having an average effective diameter between 0.1 and 6 microns may contain individual fibers with diameters greater than 6 microns and/or individual fibers with diameters less than 0.1 micron.

"Non-biopersistent" refers to microfibers comprising at least 18% alkaline and alkaline earth oxides and meets at least one of the criteria for lack of biopersistence listed below. A non-biopersistent material according to the present invention can also meet the criteria of the German Dangerous Substances Ordinance (Gefahrstoffverordnung) Annex V, No. 7.1(1). A suitable method for selecting a fiber composition to test for non-biopersistence of certain fibers according to the test method below is to use the method reported by Eastes, W., Potter, R. M., and Hadley, J. G. (2000), "Estimation of Dissolution Rate from In-Vivo Studies of Synthetic Vitreous Fibers,"*Inhalation Toxicology,* 12(11), 1037-1054. An online calculator implementing the method can be found at http://fiberscience.owenscorning.com/kdisapp.html. This calculator predicts the rate of bio-dissolution as a function of the chemical composition of the fiber. A non-biopersistent fiber meets at least one of the following criteria: (1) a short-term biopersistence test by inhalation showing that the fibers longer than 20 um have a weighted half-life of less than 10 days (a suitable short-term biopersistence test by inhalation is described in European Union protocol ECB/TM/26 rev. 7), or (2) a short-term biopersistence test by intratracheal instillation showing that the fibers longer than 20 um have a weighted half-life less than 40 days (a suitable short-term biopersistence test by intratracheal instillation is described in European Union protocol ECB/TM/27 rev. 7), or (3) an appropriate intraperitoneal test showing no evidence of excess carcinogenicity (a suitable test for carcinogenicity of inorganic vitreous microfibers after intra peritoneal injection in rats is described in European Union protocol ECB/TM/18(97)), or (4) a suitable long-term inhalation test showing the absence of relevant pathogenicity or neoplastic changes (A suitable long-term inhalation test is described in European Union protocol ECB/TM/17(97)). These test methods are reported in European Commission Joint Research Centre Institute for Health and Consumer Protection Unit: Toxicology and Chemical Substances, European Chemicals Bureau (1999), "Methods for the Determination of the Hazardous Properties for Human Health of Man Made Mineral Fibres (MMMF)," Report 18748, David M. Bernstein and Juan M. Riego Sintes Eds.

As used herein, the term "superabsorbent" refers to a material capable of absorbing at least ten times its dry weight of a 0.9% saline solution at 25° C. Superabsorbent polymers, without being bound by theory, may absorb fluid via an osmotic mechanism to form a gel. Superabsorbents may be particulates, fibers, foams, sheets, or other shapes.

As used herein, the term "symmetry" refers to an exact correspondence of form and constituent configuration on opposite sides of a dividing line or plane or about a center or an axis.

An absorbent article according to the present invention comprises a liquid permeable topsheet; a liquid impermeable backsheet joined to the topsheet and an absorbent core disposed between the topsheet and the backsheet. The absorbent core comprises a first absorbent core having a upper surface, a first area and a second area wherein the first area and the second area are horizontally arranged and the second area has a lower absorption capacity than the first area, and a second absorbent core having a periphery. The first absorbent core and the second absorbent core are different from each other at least in one property selected from the group consisting of composition, density or absorption capacity, opacity, color, flexibility, or resistance to compression or bunching. In one embodiment, an absorbent article according to the present invention may be designed to have a predictable body fit when worn and to have a second core with higher flexibility and/or resistance to bunching than a first core which may reduce soiling and/or fluid leakage. Flexibility can be provided by employing a different core material or forming holes or slits on a core. In another embodiment, an absorbent article according to the present invention may be designed to have better color/strain control in a second core. The first absorbent core and the second absorbent core are vertically arranged, and the second absorbent core at least partially covers a upper surface of the second area of the first absorbent core. The second area can be a void area.

Referring to FIG. 1A, the absorbent article 10 has a longitudinal axis L and a transverse axis T that meet at a central point C. The absorbent article 10 has a front point F and a back point B. The transverse axis T is located by taking the midpoint between the absorbent article front point F and the back point B.

The absorbent article may also be provided with additional features commonly found in sanitary napkins, including "wings" or "flaps" 60 as is known in the art.

The absorbent article may also has a secondary topsheet, often called acquisition and/or distribution layer, between the topsheet and the absorbent core to promote fluid transport from the topsheet to the absorbent core. The absorbent article may further comprise a lotion composition and/or various visual signals, indicia, or other markings provided for example onto at least one of either upper or lower side of the topsheet, the absorbent core, the backsheet and/or any optional layer.

In one embodiment, referring to FIG. 1A, and FIGS. 1B and 1C, cross section views of the absorbent article 10 shown in FIG. 1A by section 1B-1B and section 1C-1C, respectively, the absorbent article 10 has a topsheet 20 having an upper surface 32 and lower surface 35 opposite the upper surface 32, a liquid impervious backsheet 30 joined to the topsheet 20, and an absorbent core 40 disposed between the topsheet 20 and the backsheet 30. The backsheet 30 has an upper surface 43 and a lower surface 44 opposite the upper surface 43. The absorbent article 10 has an adhesive 82 on the lower surface 44 of the backsheet 30. The absorbent core 40 has a first absorbent core 41 comprising a first area 411 and a second area 421, and a second absorbent core 42. The second absorbent core 42 is disposed to at least partially overlap in its periphery 66 with the second area 421 in a transverse direction of the first absorbent core 41. The first absorbent core 41 contains an upper surface 46, a lower surface 48 opposite the upper surface 46, a first area 411 and a second area 421. The second absorbent core 42 contains an upper surface 36 and a lower surface 38 opposite the upper surface 36. The upper surface 36 of the second absorbent core 42 may be in direct contact with the lower surface 35 of the topsheet 20. The lower surface 38 of the second absorbent core 42 is in contact with the upper surface 46 of the first absorbent core 41. The lower surface 48 of the first absorbent core 41 is in contact with the upper surface 44 of the backsheet.

Figure 4A:
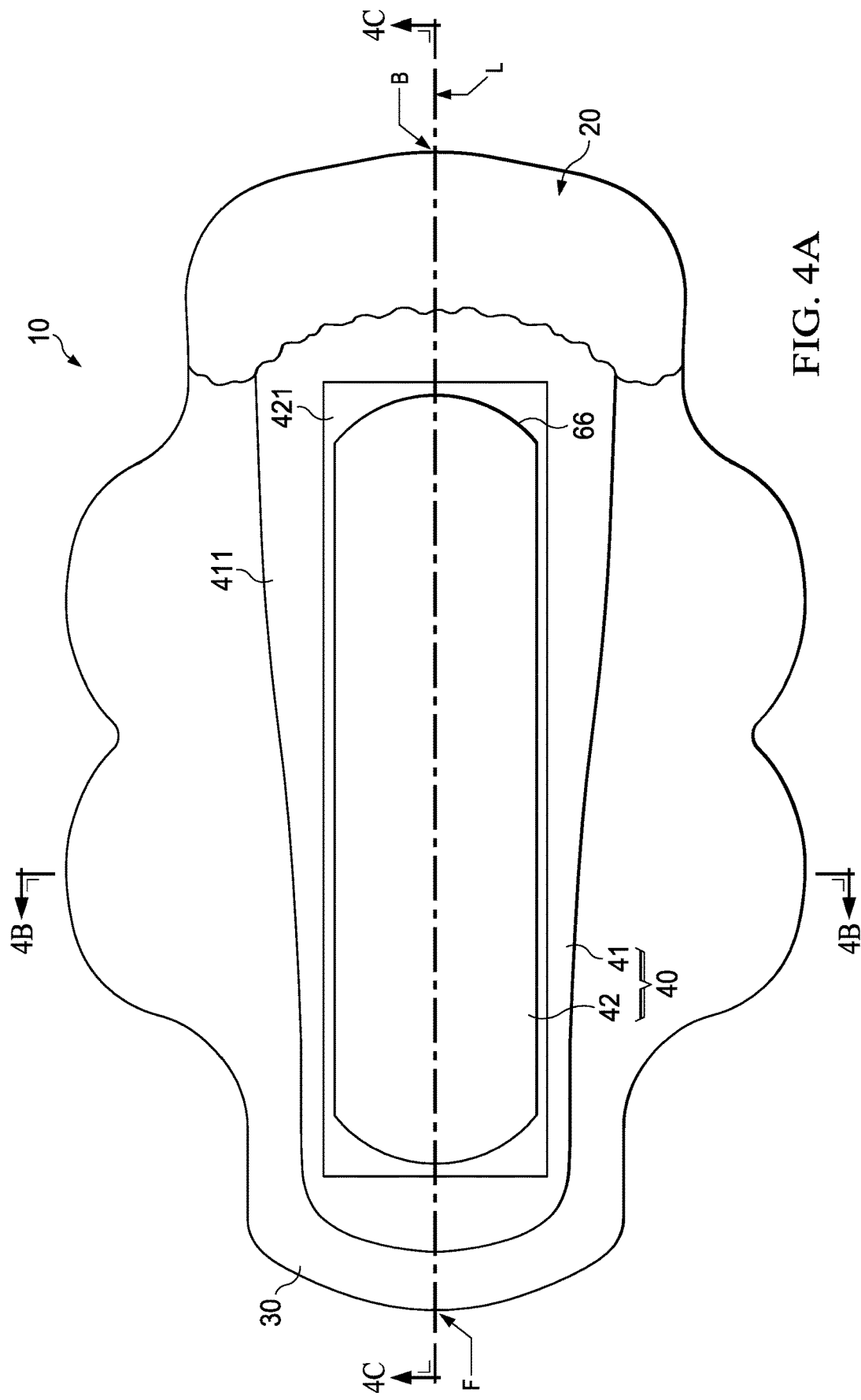
FIG. 4A is a plan view of another embodiment of an absorbent article according to the present invention.

In another embodiment, referring to FIG. 4A, and FIG. 4B and FIG. 4C which are cross section views of the absorbent article 10 shown in FIG. 4A, a second absorbent core 42 is disposed to overlap in its entire periphery 66 with a second area 421 of a first absorbent core 41. The second area 421 of the first absorbent core 41 is a void area, and a lower surface 48 of the first absorbent core 41 may be in directly contact with a upper surface 43 of a backsheet 30.

Figure 5A:
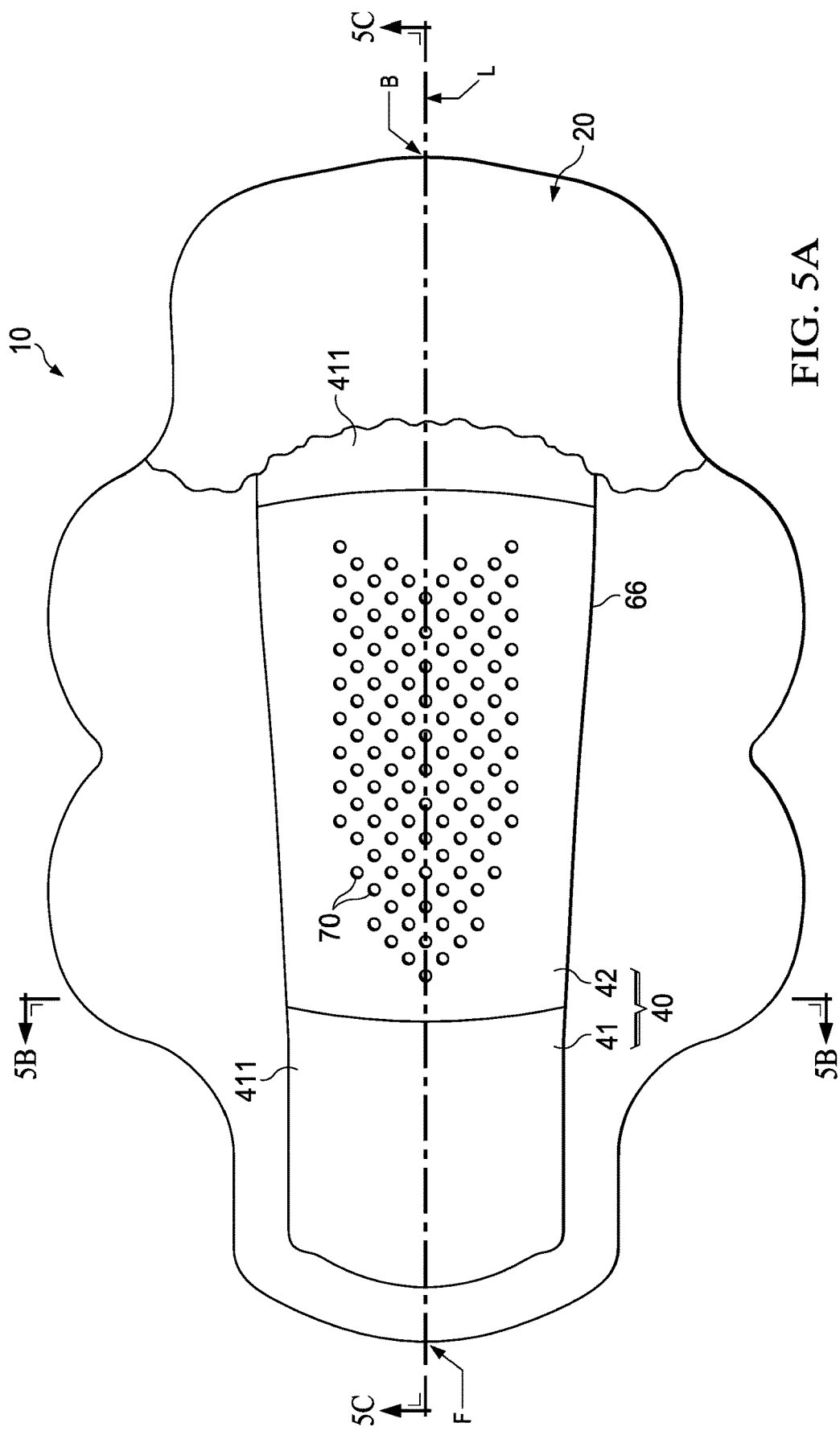
FIG. 5A is a plan view of another embodiment of an absorbent article according to the present invention.

In another embodiment, referring to FIG. 5A, and FIG. 5B and FIG. 5C which are cross section views of the absorbent article 10 shown in FIG. 5A, the second absorbent core 42 is disposed to completely cover an upper surface of the second area 421 of the first absorbent core 41, and partially overlaps in its periphery 66 with the first area 411. In the embodiment, the second area 421 of the first absorbent core 41 is a void area surrounded with the first area 411 on at least one side in a transverse direction.

In another embodiment as a variation of the embodiment shown in FIGS. 5A, 5B and 5C, the second area 421 of the first absorbent core 41 comprises a conventional core material explained under ABSORBENT CORE below.

Figure 6A:
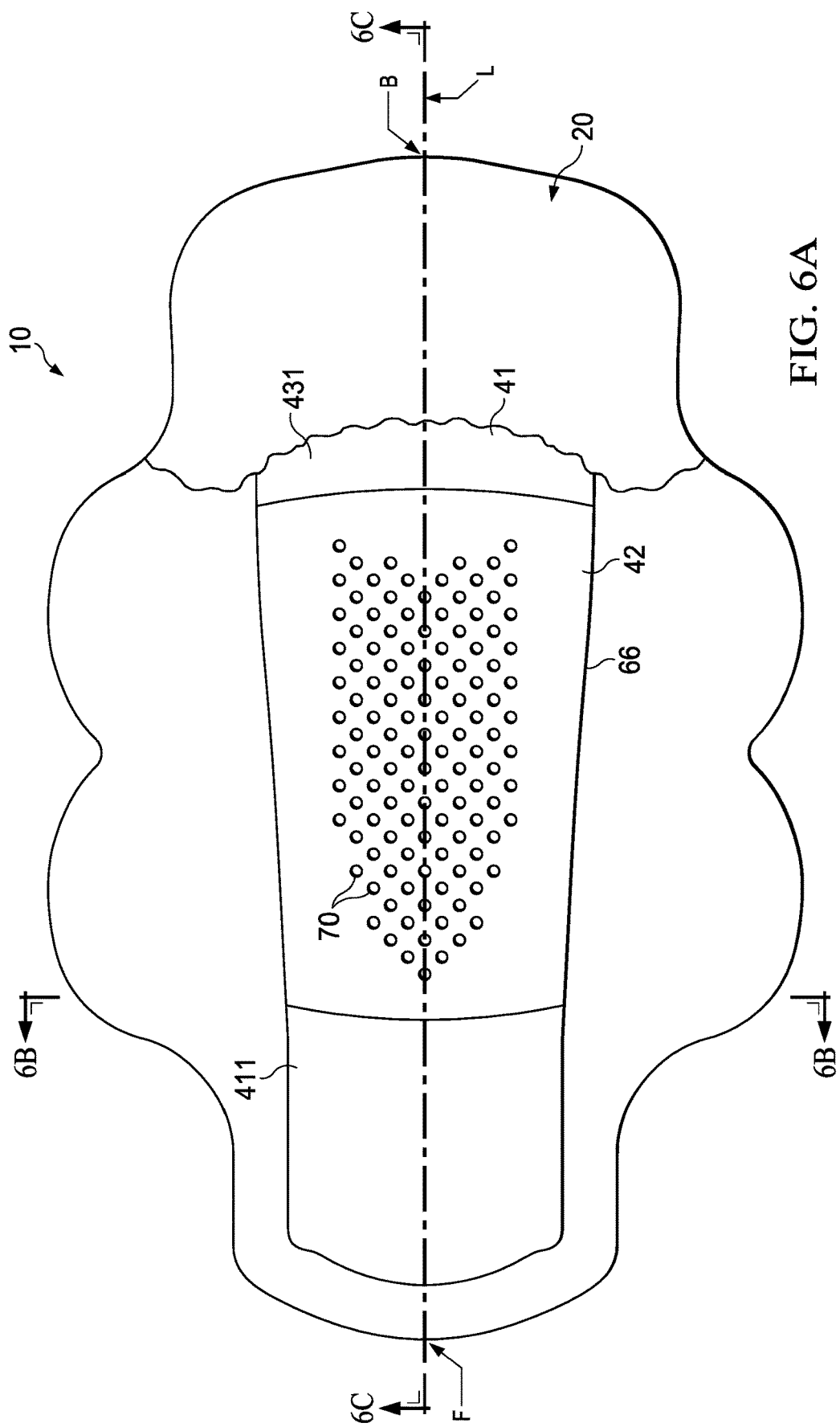
FIG. 6A is a plan view of another embodiment of an absorbent article according to the present invention.

In another embodiment, referring to FIG. 6A, and FIG. 6B and FIG. 6C which are cross section views of the absorbent article 10 shown in FIG. 6A, the first absorbent core 41 further comprises the third area 431 in addition to the first area 411 and the second area 421. The three areas may be arranged horizontally in a longitudinal direction where the second area 421 is sandwiched between two side areas of 411 and 431. The first area 411 and the third area 431 may be identical, or may differ from each other at least in its composition, density or absorption capacity.

In a similar way, when the first absorbent core 41 comprises three areas in a transverse direction where the second area 421 is sandwiched between two side areas, both sides outside of the second area 421 in a transverse direction can be first areas 411, or one side is a first area 411 and the other side is a third area 431. The first area 411 and the third area 431 may be identical areas, or may differ from each other at least in composition, density or absorption capacity.

Figure 7A:
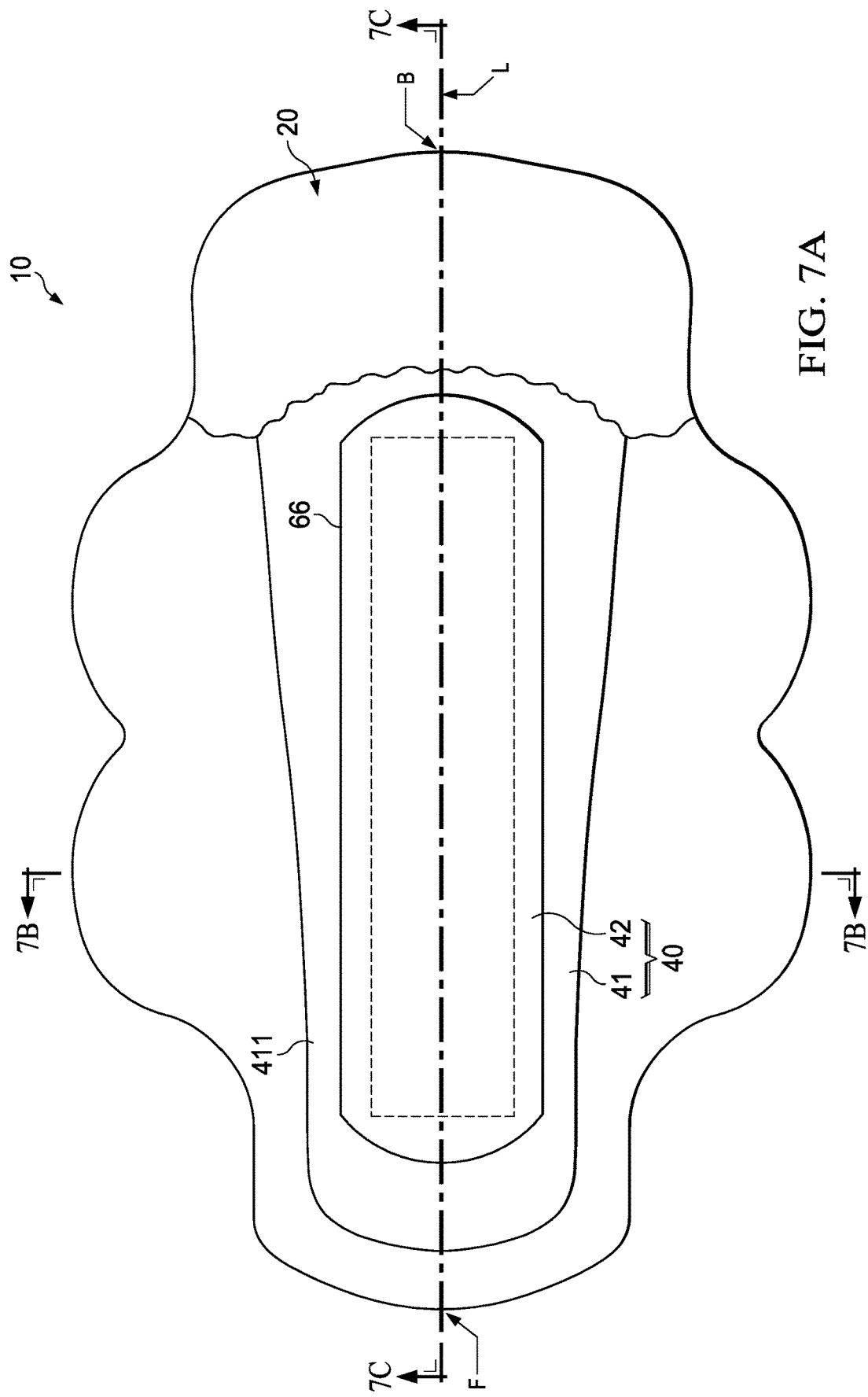
FIG. 7A is a plan view of another embodiment of an absorbent article according to the present invention.

In another embodiment, referring to FIG. 7A, and FIG. 7B and FIG. 7C which are cross section views of the absorbent article 10 shown in FIG. 7A, the second absorbent core 42 is disposed to completely cover the entire upper surface of second area 421 of the first absorbent core 41, and overlaps in substantially the entire periphery 66 with the first area 411 of the first absorbent core 41. In the embodiment, the second area 421 of the first absorbent core 41 is a void area, and it is surrounded by the first area 411. In another embodiment as a variation of the embodiment shown in FIG. 7A, the second area 421 of the first absorbent core 41 comprises a conventional core material explained under ABSORBENT CORE below.

Topsheet

A topsheet in the present invention can be any known or otherwise effective topsheet material, provided that the material has appropriate liquid permeability and smoothness to the skin. The topsheet can be a polymeric film, a nonwoven, a woven fabric, a paper web, a tissue paper web, a cellulosic web or a knitted fabric, or a multilayer laminate of any of the aforementioned.

Polymeric films suitable for the topsheet can comprise thermoplastic polymers having characteristic rheological properties which depend on their composition and temperature. Polymeric films can include materials normally extruded or cast as films such as polyolefins, nylons, polyesters, and the like. Such films can comprise thermoplastic materials such as polyethylene, low density polyethylene, linear low density polyethylene, polypropylenes and copolymers and blends containing substantial fractions of these materials. Such films can be treated with surface modifying agents to impart hydrophilic or hydrophobic properties, such as imparting a lotus effect. Polymeric films can be textured or otherwise altered by forming macro feature and/or micro features from a strictly flat, planar configuration. As used in the present specification, macro features are elements that are visible to the unaided eye of a person having 20/20 vision from a distance of 30 cm in lighting at least equal to the illumination of a standard 100 watt incandescent white light bulb. Micro features are elements that are not visible to the unaided eye of a person having 20/20 vision from a distance of 30 cm in lighting at least equal to the illumination of a standard 100 watt incandescent white light bulb, wherein the illumination source is within 10 ft and vertically above the viewing surface.

Nonwovens suitable for the topsheet can comprise unbonded fibers, entangled fibers, tow fibers, or the like. Fibers can be extensible and/or elastic, and may be pre-stretched for processing. Fibers of the nonwoven can be continuous, such as those produced by spunbonded methods, or cut to length, such as those typically utilized in a carded process. Fibers can be absorbent, and can include fibrous absorbent gelling materials. Fibers can be bicomponent, multiconstituent, shaped, crimped, or in any other formulation or configuration known in the art for nonwoven webs and fibers.

Nonwovens suitable for the topsheet can be any known nonwovens comprising polymer fibers having sufficient elongation properties to form macro features and/or micro features on the nonwoven.

In general, the polymeric fibers can be bondable, either by chemical bond (e.g. by latex or adhesive bonding), pressure bonding, or thermal bonding. Nonwovens for the topsheet can comprise about 100% by weight thermoplastic fibers. Nonwovens for the topsheet can comprise as little as about 10% by weight thermoplastic fibers.

A laminate suitable for the topsheet can comprise two or more nonwoven or a combination of polymer films, nonwoven, woven fabrics, paper webs, tissue webs, or knitted fabrics. Not to be limiting, a laminate topsheet can comprise two layers of film, two layers of nonwoven, or a layer of nonwoven with a film.

The topsheet of an absorbent article according to the present invention can have various optional characteristics, as is known in the art. For example, the topsheet can have channels embossed or other textured surfaces therein to direct fluid flow. The topsheet may also have macro features and/or micro features such as apertures and tufts. Referring to FIG. 1A, apertures 24 can serve the additional benefit of capturing fluid and fluid components that would otherwise tend to run off of the absorbent article 10 and possibly soil the garments of the wearer. For example, if fluid were to run off toward the longitudinal end of the absorbent article 10, apertures 24 could intercept the fluid as it progressed, permitting a relatively unobstructed passage to an underlying absorbent core 40. These apertures 24 may also serve as indicia regarding the placement of the absorbent article 10 regarding the pudendal region and the undergarment.

Backsheet

A backsheet of an absorbent article according to the present invention can be any known or otherwise effective backsheet material, provided that the backsheet prevents external leakage of exudates absorbed and contained in the absorbent article. Flexible materials suitable for use as the backsheet include, but are not limited to, woven and nonwoven materials, laminated tissue, polymeric films such as thermoplastic films of polyethylene and/or polypropylene, composite materials such as a film-coated nonwoven material, or combinations thereof.

Absorbent Core

An absorbent core in the absorbent article according to the present invention comprises a first absorbent core comprising a first area and a second area wherein the second area has a lower absorption capacity than the first area, and a second absorbent core having a periphery. The first absorbent core and the second absorbent core are vertically arranged, and the second absorbent core at least partially covers the second area of the first absorbent core.

As explained in the section of First Absorbent Core below, a second area of a first absorbent core may comprise a void area. A void area herein means an area empty and with no component of an absorbent article.

When a second area is a void area and the second absorbent core is configured to be placed within the void area, the configuration of the first absorbent core and the second absorbent core is still considered being vertically arranged.

Referring to FIG. 1A, the absorbent core 40 can have additional features in the first absorbent core 41, the second absorbent core 42, or both the first and second absorbent cores. Additional features in the absorbent core 40 may include slits, slots, apertures and lateral stiffeners.

The first absorbent core 41 and/or the second absorbent core 42 can have a plurality of laterally-oriented slots 72 having an average gap width of at least 1 mm prior to use. Slots 72 are considered laterally oriented if they have a major vector component at the longitudinal center line L that is perpendicular to the longitudinal center line. Slots 72 can be substantially parallel, generally linear slots that are each parallel to center line L, and, therefore, have no vector component in the longitudinal direction. However, slots 72 can have other configurations, including generally curved orientations. The first absorbent core 41 and/or the second absorbent core 42 may also have any number of holes 70. Absorbent core 40 can have additional modifications and features to facilitate desired bending and folding. For example, absorbent core 40 can have additional slits, apertures, perforations, lines of weakness, lateral stiffeners, and the like. In particular, in one embodiment a line of weakness such as perforations or a score line along at least a portion of the longitudinal center line L can aid in proper formation of a raised hump or protrusions intended to improve skin contact in that are of the absorbent article.

First Absorbent Core

A first absorbent core comprises a first area and a second area having a lower absorption capacity than the first area. Herein, "lower absorption capacity" includes zero absorption capacity like the case when the second area is a void area as explained below. The first absorbent core may be in any geometric shape commonly known.

A first area and a second area of a first absorbent core are horizontally arranged. The surface area of the first absorbent core herein means the entire surface area of an upper surface of the first area and an upper surface of the second area.

The second area of the first absorbent core may comprise a void area. When the second area comprises a void area, an area empty with no component of an absorbent article, the void area is considered to have a virtual upper surface and lower surface extended from a upper surface and a lower surface of the first area, respectively. When a second area is a void area, the void area has a central point C within the void area. The void area is at least partially surrounded by a non-void area such as a first area of the first absorbent core.

A first absorbent core may further comprise a third area which may differ from the first area at least in its composition, density or absorption capacity. When the first absorbent core has a third area, the third area may differ from the second absorbent core at least in its composition, density or absorption capacity.

Figure 2A:
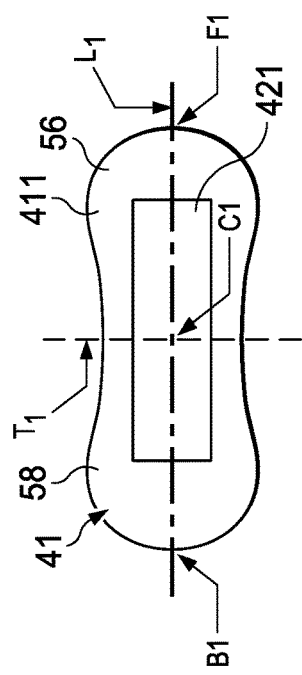
FIG. 2A is a plan view of an example of a first absorbent core of an absorbent core of an absorbent article according to the present invention.
Figure 2B:
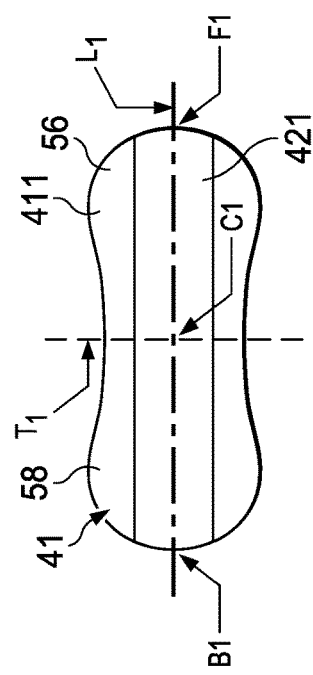
FIG. 2B is a plan view of another example of a first absorbent core of an absorbent core of an absorbent article according to the present invention.

FIG. 2A and FIG. 2B show exemplary embodiments of the first absorbent core 41. Referring to FIG. 2A and FIG. 2B, the first absorbent core 41 of an absorbent core 40 comprises a first area 411 and a second area 421, and has a longitudinal axis L1 and a transverse axis T1 that meet at a central point C1. The transverse axis T1 is located by taking the midpoint between the front point F1 and the back point B1 outermost periphery points of the first absorbent core 41. T1 may overlay T. L1 may overlay L.

The first absorbent core 41 is approximately no greater than 25000 mm$^2$, 16000 mm$^2$ 9000 mm$^2$, 4000 mm$^2$, 1000 mm$^2$, or even less total surface area on any one surface, such as, for example approximately 2500 mm². Alternatively, the first absorbent core covers no greater than 95%, 90%, 85%, 80%, 75%, 70%, 65%, 60%, 55%, 50%, 45%, 40%, 35%, 30%, 25%, 20%, 15%, or 10% of the backsheet 30. First absorbent core 41 is divided by T1 into first absorbent core section one 56 and first absorbent core section two 58. First absorbent core section one 56 and first absorbent core section two 58 may be asymmetric or symmetric relative to transverse center line T1. First absorbent core section one 56 may be equal to, wider than or narrower than second absorbent core section two 58.

The first absorbent core can be formed from any suitable materials. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers.

The first absorbent core can be made by air-laying the mixture of fibers and thermoplastic material. In general, air-laying can be carried out by metering an airflow containing the fibers and thermoplastic material, in substantially dry condition, onto a typically horizontally moving wire forming screen. Suitable systems and apparatus for air-laying mixtures of fibers and thermoplastic material are disclosed in, for example, U.S. Pat. No. 4,157,724 (Persson), issued Jun. 12, 1979, and reissued Dec. 25, 1984 as Re. 31,775; U.S. Pat. Nos. 4,278,113; 4,264,289; 4,352,649; 4,353,687; 4,494,278; 4,627,806; 4,650,409; and 4,724,980.

The first absorbent core may be specially designed to work synergistically with the higher absorption performing second absorbent core while minimizing the spread of fluid away from the second absorbent core and towards the perimeter of the product.

The first absorbent core may comprise airlaid material. A method of producing an absorbent core comprising airlaid material is disclosed, for example, in U.S. Pat. No. 8,470,219. For example, cellulose fibers are continuously deposited by a hammer mill by a first former onto a conveyor belt as loose fleece, so that a layer of tangled cellulose fibers is produced. A further preformed cellulose fiber layer may be deposited by a second former as a layer, and a third layer may be placed on by a third former. The individual fiber layers may also comprise different fibers and varying fiber densities. Moreover, it is possible to add superabsorbent polymers to the fibers to increase the absorption capacity. The superabsorbent polymer may also be added to the fibers homogeneously prior to the sprinkling. These cellulose fiber layers are still uncompressed to a large extent. These are commercial products which have been used in the hygiene field for some time and which have already been described. Superabsorbent polymer may be added in designated zones or lanes. For example, superabsorbent polymer can be added in the first area 411 and the second area 421 of the first absorbent core in different concentrations, or can be added in the first area 411 only. Selective addition of superabsorbent polymer can be achieved by a number of ways known to the art, like having two separate superabsorbent polymer guns and/or nozzles in the same or different superabsorbent polymer enclosures, or having one superabsorbent polymer gun/nozzle and having baffles internal or external to direct the superabsorbent polymer stream into multiple distinct lanes/zones. A compression of cellulose fiber layer(s) for example by embossment is followed. Cellulose fiber layers or superabsorbent polymer can be disposed in such a designated area on a belt that will be a first area of a first absorbent area.

The first absorbent core may feature two distinct density zones. The first density zone is a low density acquisition zone designed to minimize after use fluid appearance differences with the second absorbent core. Below this upper acquisition zone is a second density zone for mainly fluid storage that comprises of a higher density than the lower density acquisition zone. The density of the second density zone is preferably between 1.5 times and 3 times the density of the first density zone. Even more preferred is a second density zone that is between 2 times and 3 times the density of the first density zone.

In a non-limiting embodiment, the airlaid material may comprise at least one BiCo fiber. The BiCo fiber may be a thickness of about 3 DTex to 5 DTex, provided that the BiCo provides appropriate integrity and volume to the airlaid core.

Together the use of two BiCo fibers provides wet integrity to the overall airlaid core material while allowing the final acquisition zone density to be controlled.

To ensure fluid not retained by the second absorbent core absorbent material is sufficiently contained within the first absorbent core material, the first absorbent core, at least in the first area, may have superabsorbent polymers. Contents of superabsorbent polymer in the first area and the second area of the first absorbent core can be determined depending on product design, and may different in the first area and the second area. The first area may contain superabsorbent preferably at least 5%. The second area may contain less than 5% superabsorbent material by weight of the first absorbent core material, preferably substantially no superabsorbent.

In one embodiment, the first absorbent core may have substantially no superabsorbent polymer within 10 mm, preferably 5 mm, either outward or inward direction from the periphery of the second absorbent core.

Second Absorbent Core

Figure 3:
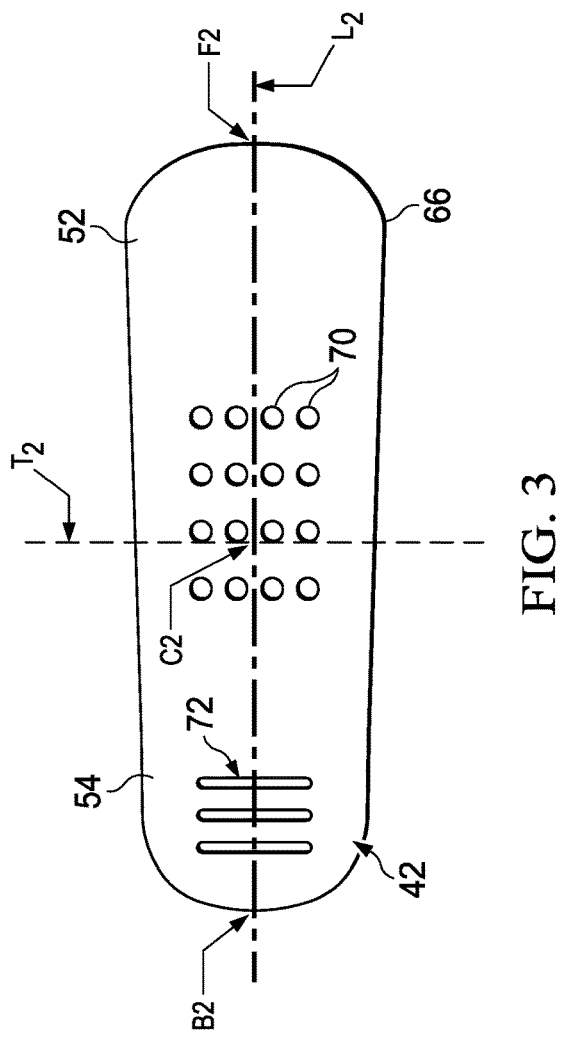
FIG. 3 is a plan view of an example of a second absorbent core of an absorbent core of an absorbent article according to the present invention

Referring to FIG. 3, the second absorbent core 42 has a longitudinal axis L2 and a transverse axis T2 that meet at a central point C2, and a periphery 66. The transverse axis T2 is located by taking the midpoint between the front point F2 and the back point B2 outermost periphery points of the second absorbent core 42. The transverse axis T2 may or may not overlay T and/or T1. Similarly, the longitudinal axis L2 of the second absorbent core 42 may or may not overlay the longitudinal axis L1 of the first absorbent core 42 and/or the absorbent article longitudinal axis L.

The second absorbent core may cover no greater than 10%, 15%, 20%, 25%, 30%, 35%, 40%, 45%, 50%, 55%, 60%, 65%, 70%, 80%, 85%, 90%, or 95% of a upper surface of the first absorbent core. Alternatively, the second absorbent core may be covered by no greater than 95%, 90%, 85%, 80%, 75%, 70%, 65%, 60%, 55%, 50%, 45%, 40%, 35%, 30%, 25%, 20%, 15%, or 10% of a lower surface of the topsheet. The ratio of the second absorbent core to a upper surface of the first absorbent core or to the lower surface of the topsheet can vary depending on size and/or shape of the first and/or second absorbent core, product shape, product size, the presence of wings, etc.

Second absorbent core 42 is divided by a transverse axis T2 into second absorbent core section one 52 and second absorbent core section two 54. First absorbent core section one 52 and first absorbent core section two 54 may be asymmetric or symmetric relative to the transverse center line T2. Second absorbent core section one 52 may be equal to, wider than or narrower than second absorbent core section two 54.

The second absorbent core 42 can be either asymmetric or symmetric relative to the transverse center line T2. T2 may also be located 10 cm, 8 cm, 6 cm, 5 cm, 4 cm, 3 cm, 2 cm or 1 cm away from T or T1 along the longitudinal center line L2 towards the front or back of the absorbent article.

The second absorbent core 42 may be made of any material provided that it exhibits an absorption capacity higher than either the second area 421 or the first area 411 of the first absorbent core 41.

In a non-limiting example, the second absorbent core 42 can include open celled foam. One exemplary open-celled foam, High Internal Phase Emulsion (HIPE) foam, is produced from the polymerization of the monomers including the continuous oil phase of a HIPE. HIPE foams may have one or more layers, and may be either homogeneous or heterogeneous polymeric open-celled foams. Homogeneity and heterogeneity relate to distinct layers within the same HIPE foam, which are similar in the case of homogeneous HIPE foams or which differ in the case of heterogeneous HIPE foams. A heterogeneous HIPE foam may contain at least two distinct layers that differ with regard to their chemical composition, physical properties, or both; for example layers may differ with regard to one or more of foam density, polymer composition, specific surface area, or pore size (also referred to as cell size). For example, for a HIPE foam if the difference relates to pore size, the average pore size in each layer may differ by at least 20%, by at least 35%, and by at least 50%. In another example, if the differences in the layers of a HIPE foam relate to density, the densities of the layers may differ by at least 20%, by at least 35%, and by at least 50%. For instance, if one layer of a HIPE foam has a density of 0.020 g/cc, another layer may have a density of at least 0.024 g/cc or less than 0.016 g/cc, in certain embodiments at least 0.027 g/cc or less than 0.013 g/cc, and in still other embodiments at least 0.030 g/cc or less than 0.010 g/cc. If the differences between the layers are related to the chemical composition of the HIPE or HIPE foam, the differences may reflect a relative amount difference in at least one monomer component, for example by at least 20%, in certain embodiments by at least 35%, and in still further embodiments by at least 50%. For instance, if one layer of a HIPE or HIPE foam is composed of 10% styrene in its formulation, another layer of the HIPE or HIPE foam should be composed of at least 12%, and in certain embodiments of at least 15% styrene.

The use of a foam second absorbent core 42 that is smaller in total surface of the absorbent core 40 provides a higher absorbency area only where it is needed the most, rather than on the entire surface of the absorbent core 40. This enables cost savings since foam which is relatively expensive is only used where it makes the biggest absorbency performance impact. The use of a smaller second absorbent core 42 may also act as a signal for improved placement. The creation of a visible second absorbent core 42 that is smaller in surface area than the first absorbent core 41 allows the consumer to use the second absorbent core as a marker to determine proper placement. For instance, a user can place the absorbent article in the undergarment such that the second absorbent core 42 lines up with the user's pudendal region.

A HIPE foam having separate layers formed from differing HIPEs, as explained in more detail below, provides a HIPE foam with a range of desired performance characteristics. For example, a HIPE foam including a first and second foam layer, wherein the first foam layer having a relatively larger pore or cell size than the second layer, when used in an absorbent article may more quickly absorb incoming fluids than the second layer. The second foam layer having relatively smaller pore sizes, as compared to the first foam layer, which exert more capillary pressure and drain the acquired fluid from the first foam layer, restoring the first foam layer's ability to acquire more fluid. HIPE foam pore sizes may range from 1 to 200 µm and in certain embodiments may be less than 100 µm. The desired thickness of a HIPE will depend on the materials used to form the HIPE, the speed at which a HIPE is deposited on a belt, and the intended use of the resulting HIPE foam. The HIPE foam for the present invention may have a thickness of 0.8 mm to 3.5 mm.

The HIPE foams for the present invention are relatively open-celled. This refers to the individual cells or pores of the HIPE foam being in substantially unobstructed communication with adjoining cells. The cells in such substantially open-celled HIPE foam structures have intercellular openings or windows that are large enough to permit ready fluid transfer from one cell to another within the HIPE foam structure. For purpose of the present invention, a HIPE foam is considered "open-celled" if at least 80% of the cells in the HIPE foam that are at least 1 µm in size are in fluid communication with at least one adjoining cell.

In addition to being open-celled, in certain embodiments HIPE foams are sufficiently hydrophilic to permit the HIPE foam to absorb aqueous fluids, for example the internal surfaces of a HIPE foam may be rendered hydrophilic by residual hydrophilizing surfactants or salts left in the HIPE foam following polymerization, by selected post-polymerization HIPE foam treatment procedures or combinations of both.

A HIPE foam can be flexible and exhibit an appropriate glass transition temperature (Tg). The Tg represents the midpoint of the transition between the glassy and rubbery states of the polymer. In general, HIPE foams that have a higher Tg than the temperature of use can be very strong but will also be very rigid and potentially prone to fracture.

HIPE foams intended for applications requiring flexibility should contain at least one continuous region having a Tg as low as possible, so long as the overall HIPE foam has acceptable strength at in-use temperatures. In certain embodiments, the Tg of this region will be less than 30° C. for foams used at ambient temperature conditions, in certain other embodiments less than 20° C. For HIPE foams used in applications wherein the use temperature is higher or lower than ambient, the Tg of the continuous region may be no more than 10° C. greater than the use temperature, in certain embodiments the same as use temperature, and in further embodiments 10° C. less than use temperature wherein flexibility is desired. Accordingly, monomers are selected as much as possible that provide corresponding polymers having lower Tg's.

The mean cell diameters for open-celled foams can be between 10 and 1,000 microns. The mean densities of open-celled foams can be between 40 kg/m3 and 100 kg/m3. Mean cell diameters refer to the diameter of the pores in the foam visible by microscopy. The pores tend to be relatively spherical in shape and the mean diameter can be measured by using microscopic techniques. One suitable technique is to use a scanning electron micrograph and measure the apparent mean diameter of at least 25 representative cells to determine the mean. The density of foams can be determined using uncompressed samples of said foams devoid of contaminants such as water, and measuring the volume and weight of the foam. A cubic sample having an edge length greater than or equal to 2 cm is practical.

The ability of a structure to "pull" fluid against an opposing force, such as gravity or against affinity for fluid of another substrate with which the structure is in intimate capillary contact, can be characterized by the capillary pressure. The capillary pressure can be characterized as the hydrostatic head at which the vertically wicked fluid loading is 50% of the free absorbent capacity under equilibrium conditions at 31° C. The hydrostatic head is represented by a column of fluid (e.g., synthetic menses). The second absorbent core 42 can have a capillary pressure of 2 cm to 15 cm.

The open-celled foam disclosed herein can be used in an initially compressed state that expands to full volume as a function of wear time and/or fluid loading. The foam may collapse after an insult of fluid as the first absorbent core pulls fluid away from the foam.

Test

Absorption Capacity

Excise a specimen 2.54 cm×2.54 cm (1.0 in×1.0 in) or equivalent area from the longitudinal and lateral center of the core. Pour 90 mL of saline solution (0.9% NaCl in deionized water) into a 100 mL disposable Petri dish. Measure the thickness of the specimen using a digital caliper, for example model # GS-503 available from Ono Sokki Technology Inc. (USA), using a 2.54 cm diameter foot with an applied pressure of 0.69 kPa (0.1 psi). Center the specimen under the foot and lower the foot onto the specimen at approximately 2 mm/sec. Take the reading after pressure has been applied for 5 sec and report to the nearest 0.01 mm. Measure the mass of the specimen on an analytical balance and record as "dry weight" to the nearest 0.001 g. Immerse the specimen into the saline for 15.00 min±0.01 min. Using tweezers, grasp a corner of the specimen to remove it from the saline and suspend vertically to drain for 2.00 min±0.01 min. Measure the mass of the wet specimen and record as the "wet weight" to the nearest 0.001 g. Calculate the capacity as follows:

$$\text{Absorption Capacity (g/g)} = [\text{wet weight (g)} - \text{dry weight (g)}]/\text{dry weight (g)}$$

$$\text{Absorption Capacity (g/cc)} = [(\text{wet weight (g)} - \text{dry weight (g)}]/[\text{dry surface area (cm}^2) \times \text{dry thickness (cm)}]$$

Repeat for a total of 3 specimens and report as the mean to the nearest 0.01 g/g and 0.01 g/cc.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or patent application, including any patents for which priority is claimed in the application data sheet, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a longitudinal centerline, a transverse centerline and a central point where the longitudinal centerline and the transverse centerline cross, comprising;

a liquid permeable topsheet;

a liquid impermeable backsheet joined to the topsheet;

an absorbent core having an area disposed between the topsheet and the backsheet, wherein the absorbent core comprises a first absorbent core comprising an upper surface, a first area and a second area wherein the first area and the second area are horizontally arranged; wherein the second area is surrounded by the first area and wherein the second area is a void extending through the first absorbent core; and a second absorbent core wherein the second absorbent core is disposed within the void, wherein the first absorbent core has a pair of transverse ends opposite from one another, and wherein the second absorbent core has a pair of transverse ends opposite from one another, and wherein the transverse ends of the second absorbent core are disposed inboard of the transverse ends of the first absorbent core;

wherein the first absorbent core and the second absorbent core have different compositions; and wherein at least part of the first area of the first absorbent core and at least part of the second absorbent core overlap.

2. An absorbent article having a longitudinal centerline, a transverse centerline and a central point where the longitudinal centerline and the transverse centerline cross, comprising;

a liquid permeable topsheet;

a liquid impermeable backsheet joined to the topsheet;

an absorbent core having an area disposed between the topsheet and the backsheet, wherein the absorbent core comprises a first absorbent core comprising an upper surface, a first area and a second area wherein the first area and the second area are horizontally arranged; wherein the second area is surrounded by the first area and wherein the second area is a void extending through the first absorbent core; and a second absorbent core wherein the second absorbent core is disposed within the void, wherein the first absorbent core has a pair of transverse ends opposite from one another, and wherein the second absorbent core has a pair of transverse ends opposite from one another, and wherein the transverse ends of the second absorbent core are disposed inboard of the transverse ends of the first absorbent core;

wherein the first absorbent core and the second absorbent core have different compositions; and wherein the first area of the first absorbent core and the second absorbent core are configured to overlap in substantially an entire periphery of the second absorbent core.

* * * * *